United States Patent [19]

Donohue et al.

[11] Patent Number: 4,617,918
[45] Date of Patent: Oct. 21, 1986

[54] DEVICE FOR COMBINED THERAPEUTIC AND STIMULATIVE TREATMENT OF THE GUMS

[75] Inventors: John J. Donohue, Neshanic, N.J.; William J. Dunn, Libertyville, Ill.; Kedar N. Rustogi, Kendall Park, N.J.

[73] Assignee: Colgate-Palmolive Company, New York, N.Y.

[21] Appl. No.: 657,287

[22] Filed: Oct. 3, 1984

Related U.S. Application Data

[63] Continuation-in-part of Ser. No. 392,975, Jun. 28, 1982, abandoned.

[51] Int. Cl.$^4$ ............................................. A61H 9/00
[52] U.S. Cl. ...................................... 128/66; 433/90; 604/218; 604/311
[58] Field of Search ...................... 433/80, 81, 82, 89, 433/90; 604/38, 148, 183, 187, 200, 218, 232, 311; 401/264, 272, 273; 128/66

[56] References Cited

U.S. PATENT DOCUMENTS

| | | | |
|---|---|---|---|
| 2,287,209 | 6/1942 | Weiss | 401/264 |
| 2,754,590 | 7/1956 | Cohen | 433/90 |
| 3,277,894 | 10/1966 | Alexander | 604/218 |
| 3,724,076 | 4/1973 | Schmitz | 433/90 |
| 4,386,911 | 6/1983 | Maloney et al. | 433/82 X |

FOREIGN PATENT DOCUMENTS 1566628  4/1970  Fed. Rep. of Germany ...... 604/200

*Primary Examiner*—Robert P. Swiatek
*Attorney, Agent, or Firm*—Herbert S. Sylvester; Murray M. Grill; John A. Stemwedel

[57] ABSTRACT

A device for delivering an irrigant and/or a medicament fluid to the gingival sulcus comprises an elongated handle member terminating in a flexible tip portion provided with aperture(s), the tip being connected to a fluid reservoir via a conduit and operable to discharge the fluid through the apertures only on the application of pressure to the reservoir and/or opening of a normally closed valve or apertures in the tip by flexing the tip, e.g., by pressing same against a tooth. In preferred embodiments, the handle is tubular, the distal end portion thereof comprising the fluid reservoir.

3 Claims, 9 Drawing Figures

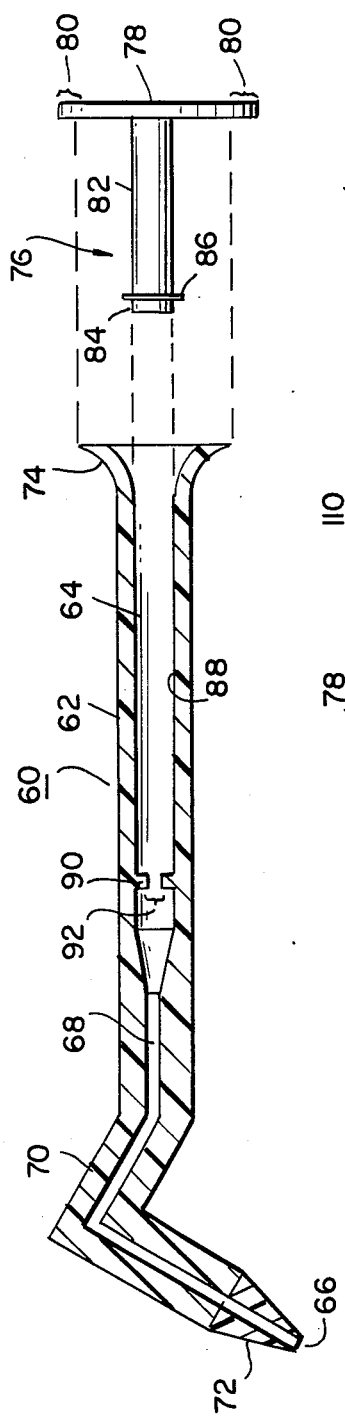
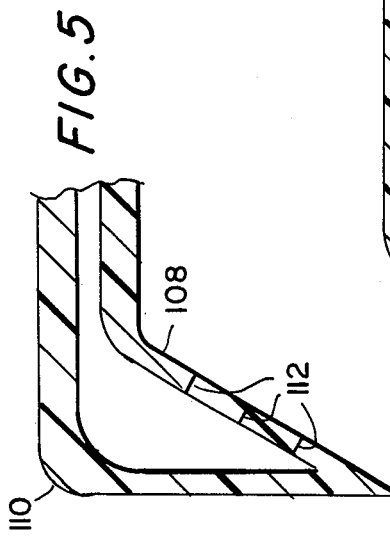
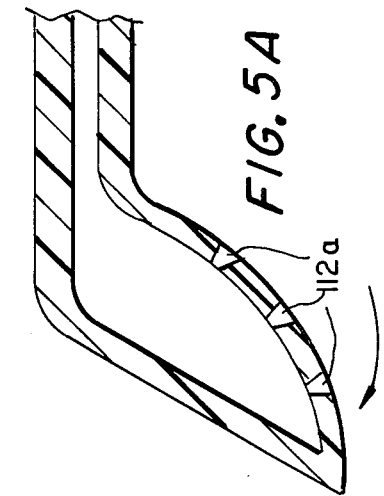
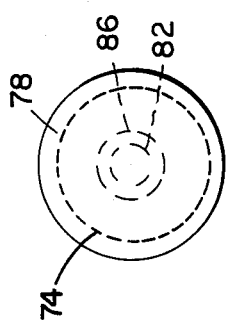
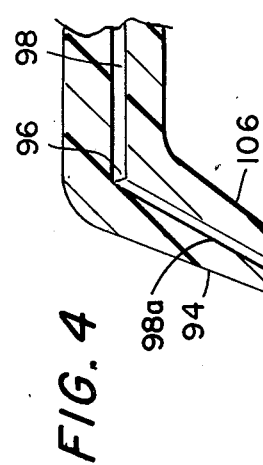

DEVICE FOR COMBINED THERAPEUTIC AND STIMULATIVE TREATMENT OF THE GUMS

This application is a continuation-in-part of our co-pending application Ser. No. 392,975, filed June 28, 1982, now abandoned.

FIELD OF INVENTION

This invention relates to a device for the combined therapeutic and stimulative treatment of the gums and especially to a device which enables the efficient delivery of an irrigant and/or a medicament liquid to the gingival sulcus and the rinsing away of oral debris from such sites as well as a method for treating the gums using such device.

DISCUSSION OF THE PRIOR ART

Devices for delivering an irrigant and/or a medicament liquid to the gums for treatment of pyorrhea and related gum disease as described in the prior art generally include a handle portion terminating in a tip portion configured to facilitate access to the gingival sulcus. As described in U.S. Pat. No. 1,586,302, the tip portion is provided with a groove for receiving a syringe whose fluid discharge is directed by said groove to one or more outlet apertures provided in the tipmost portion in contact with the gum area to be treated. Apparently, the device is manipulated to position the tip portion within the oral cavity as determined, at which point the syringe is introduced as indicated. The risk of gum injury with such a device is clear. The precise positioning of two separate devices is required under difficult conditions, particularly so as regards the syringe.

The dental injection tubes described in U.S. Pat. Nos. 1,538,797 and 1,538,798 comprise a bulbous fluid containing central portion necked down to provide an elongated tip portion. Fluid discharge is effected by hand squeezing the fluid portion. As fluid becomes depleted, increased pressures are necessary to expel fluid; the risk of gum injury as unavoidable since erratic hand movement attendant to physical strain is likely. Moreover, increased takeup of air by the fluid may severely impair the fluid's effectiveness.

The dental tool described in U.S. Pat. No. 1,015,039 for delivering coolant water to a wax inlay impression being taken in the oral cavity comprises an elongated tubular handle containing an internally disposed collapsible cartridge containing coolant fluid. The proximal cartridge end is in fluid flow contact with a proximal tip portion provided with apertures. A metal strip which overlies the cartridge is integral with an external compression member; compressive force on the latter is transmitted through the metal strip collapsing the cartridge forcing fluid through the apertured tip. The cartridge is refilled in fountain pen-like manner through the tip portion by first pressing and then releasing the compression member. The device is not designed for access to the gingival sulcus or for distributing therapeutic agent. When the compression member is released from a compressed condition, air is necessarily taken up. The method of applying pressure is awkward and inefficient since a relatively large area is involved and local pressure valves may vary.

Treatment of the teeth to remove calculus using aqueous solutions containing N-monochloroglycine either as a mouthwash or as applied by a pulsating water jet apparatus such as a Water Pic is disclosed in U.S. Pat. No. 3,886,266. Such treatments are used to wash out decayed matter so that the affected teeth can be filled.

The use of a pulsating high pressure water jet to carry aqueous N-haloamines to decayed areas of teeth through a hypodermic needle is suggested to be an alternative to drilling out such decay in U.S. Pat. No. 3,932,605.

In the treatment of periodontal disease, it is desirable to loosen plaque in the gingival sulcus and remove it without disturbing or irritating the gum tissue. The application of rinsing solutions with pulsating, high pressure water jet devices is quite severe causing pain, bleeding and inflammation.

It is another object of the invention to provide a device which is simple and efficient to use having self-contained means for delivery of fluid under low pressure.

The foregoing objects are attained in accordance with the invention which provides a device for the combined therapeutic and stimulative treatment of the gums comprising an elongated handle member terminating proximally in a flexible tip portion provided with one or more apertures for the discharge of fluid under low pressure and configured to facilitate probing contact of the tip portion with the gingival sulcus, and conduit means connecting the tip portion with a fluid reservoir portion adapted to express its contents at a low pressure.

In one embodiment, the reservoir is of elongate construction hermetically sealed by a removable insert cap movable along the longitudinal axis of the reservoir portion by an applied force to decrease the total volume of the reservoir portion and, correspondingly, increase the pressure on the fluid contained in the reservoir.

In another embodiment, the reservoir comprises a pressurized or pressurizable unit whose flow rate is controllable.

In a preferred embodiment, the handle member is of tubular construction and forms a fluid reservoir whose internal volume is defined by the sidewalls of the handle member in conjunction with the removable insert cap, positioned to hermetically seal the distal end of the handle.

The invention is described in detail by reference to the accompanying drawings wherein like reference numerals designate similar parts throughout the views and wherein:

BRIEF DESCRIPTION OF THE DRAWINGS

FIG. 3 is a side view taken in section illustrating an additional embodiment of the invention;

FIG. 3a is a top view of an insert cap in accordance with the invention;

FIGS. 4 and 4a illustrate in vertical section, shown partly broken away, a valve actuated tip portion in accordance with the invention;

FIGS. 5 and 5a illustrate in vertical section, shown partly broken away, a valve actuated tip portion in accordance with an additional embodiment of the invention.

DETAILED DESCRIPTION OF THE INVENTION

Figure 1:
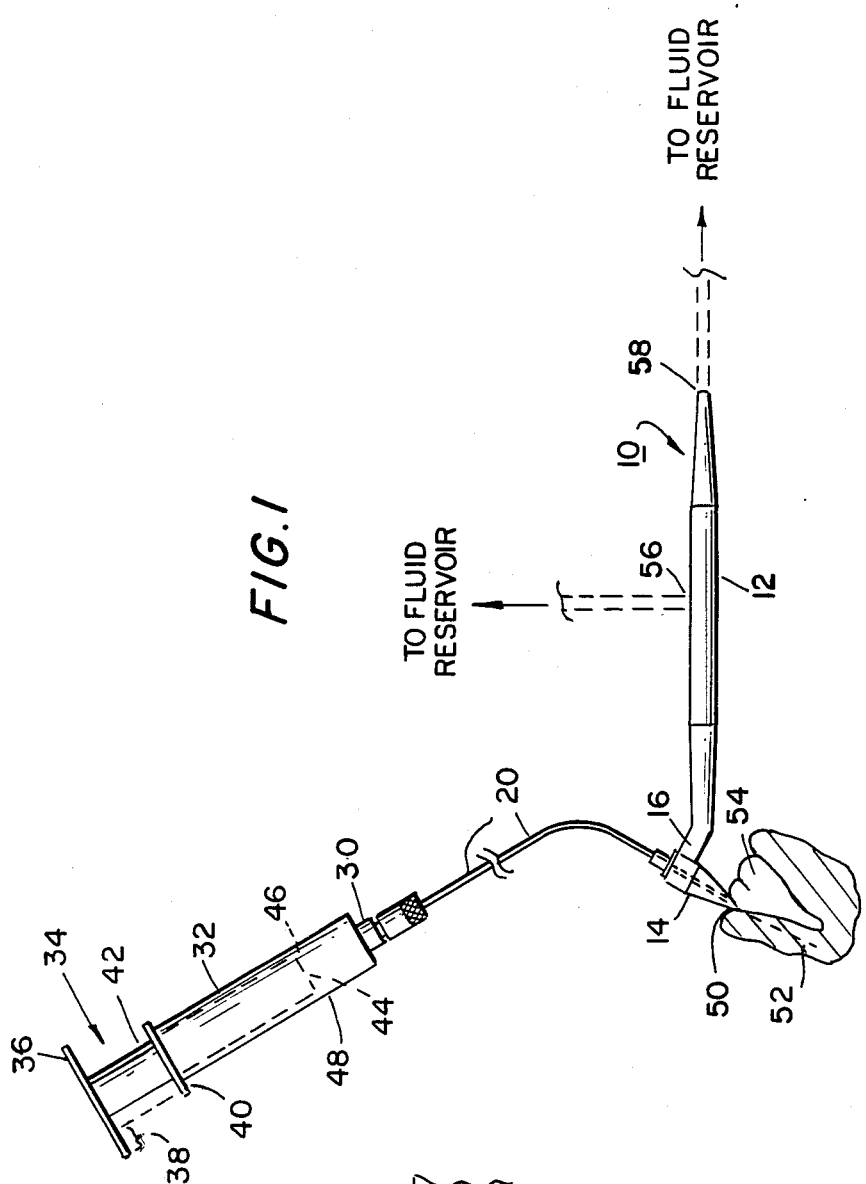
FIG. 1 schematically illustrates embodiments of the invention wherein the fluid reservoir portion comprises a physically separate member.

The present device as illustrated schematically in the embodiment of FIG. 1 comprises an elongated probe element indicated generally at 10 comprising a handle member 12 which may be of solid or tubular construction as will be explained and may be circular, rectilinear, etc., in cross section to expedite hand gripping. The probe 10 terminates proximally in a flexible tip portion 14 through a neck portion 16, angled as illustrated to facilitate positional maneuvering of the tip portion 14 within the oral cavity. As illustrated in FIGS. 2 and 2a, the tip portion 14 consists of a cylindrical neck portion 18 for fixedly receiving a conduit 20 to a depth within a channel 22 as is consistent with structural integrity. Attachment may be secured by adhesive or other suitable means, as is known. Stepped cylindrical portions 24 and 26 provide a configuration consistent with structured stability and avoid corner portions which might otherwise be injurious to the gum during use of the device. The tip portion 14 is secured to the handle member 12 via a ring portion 28 integral with the neck 16. The tip 14 coverages downwardly as illustrated at 26, terminating at the outer end 23 of the channel.

Figure 2:
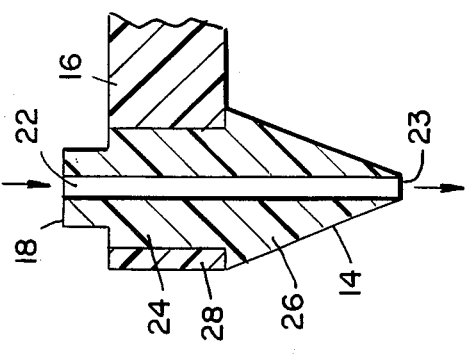
FIG. 2 is a vertical sectional view of the tip portion of FIG. 1.
Figure 2A:
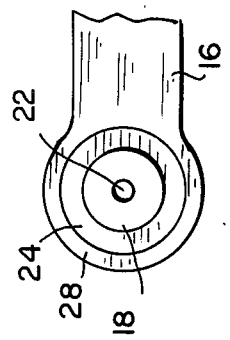
FIG. 2a is a top view (shown in full) of the tip portion of FIG. 2.

The conduit 20 connects the tip portion 14 with the outlet port 30 of a fluid reservoir 32, the latter as illustrated in FIG. 1 being a component physically separate from the probe 10 and generally comprising a syringe type device of cylindrical cross section. A removable cap insert 34 comprises a lid 36 having a diameter greater than that of the tip 40 of the reservoir 32 thus providing a peripheral portion 38 for facilitating hand removal of the cap 34, as for example, when recharging the reservoir 32. The sidewall 42 of the cap 34 is provided at its leading or lower edge portion 44 with a washer 46 sized to functionally engage at its outer vertical edge the inner surface of the sidewall 48 of the fluid reservoir 32 thereby hermetically sealing the fluid contents of the reservoir.

Use of the FIG. 1 device is as follows. Fluid such as irrigant water or medicament is charged to the fluid reservoir 32 and the cap 34 is positioned as illustrated. The diameters of the conduit 20 and the channel 22, and particularly the latter, are relatively small, to the extent that flow of charged fluid through the channel 22 is prevented principally by virtue of fluid surface tension effects unless and until the requisite pressure is applied causing downward displacement of the cap 34 along its longitudinal axis. The probe 10 is positioned in the oral cavity so that the other end of the channel portion of the tip 14 is inserted into the gingival sulcus indicated at 50 in FIG. 1, i.e., the space between the gum 52 and the tooth 54, also referred to as the tooth socket. The locus thus having been determined, the user forcibly depresses the cap 34; the application of relatively slight pressure suffices to overcome the aforementioned flow resistance thereby resulting in the discharge of fluid through the channel 22 to the determined area. In this manner, medicament or irrigant fluid is delivered at a point below the gum line.

In further embodiments, the conduit 20 may be attached to the handle member 12 at points 56 or 58 respectively as indicated by the phantom lines in FIG. 1. In such cases, the handle 12 is of tubular construction to establish a continuous flow path between the fluid point of entry and the channel 22. Distal end connection as indicated at 58 is preferable being less likely to obstruct the user's gripping or manipulation of the device.

The device may be used to the point of substantially complete exhaustion of fluid. As will be apparent, air present in the reservoir 32 provides a cushion sufficient to enable the cap 34 to function as a piston despite the total absence of fluid in the reservoir. In any event, the ratio of the total volume of reservoir to total volume of conduit is usually quite large and thus waste due to unused conduit fluid is insignificant.

Manipulation of the FIG. 1 device by the user requires both hands as opposed to the FIG. 3 device requiring but one hand. In the latter device generally designated 60 the handle 62 is of tubular construction the distal end portion thereof serving as the fluid reservoir 64. The latter is in fluid flow communication with the aperture 66 via the conduit 68 proceeding through the neck portion 70, angled as previously described, and then through the tip portion 72 convergent downwardly terminating in the aperture 66. The diameter of the reservoir 64 is relatively large compared to that of the conduit 68 for the reasons previously described, as well as to practically limit the length of the device. The handle 62 terminates distally in an outwardly flared or trumpeted portion 74 providing a funnel type end to facilitate charging of fluid to the reservoir 64. The insert cap 76 is similar in configuration to the cap 34 of FIG. 1 comprising a lid 78 having a diameter greater than that of the trumpeted section 74 as indicated by the dotted lines in FIGS. 3 and 3a thus providing a gripping area 80 for removal of the cap 76 from the fully closed (inserted) position. The sidewall 82 is provided at its leading or lower end portion 84 with a washer 86 having a vertical edge adapted upon insertion to functionally engage the inner surface 88 of the handle 62 to thereby hermetically seal the fluid contents of the reservoir 64 and to stabilize the position of the cap 76.

The FIG. 3 device is used as follows. Fluid of the type described is charged to the reservoir 64 in the amount desired. In the absence of pressure, fluid flow through the aperture 66 does not occur due to surface tension effects as described. The cap 76 is inserted into the reservoir 64 to a depth penetration sufficient to stabilize its placement. Some albeit minor fluid flow through the aperture 66 may occur indicating the attainment of fluid discharge pressure. The device is positioned in the oral cavity in the manner previously described using the thumb or forefinger of the gripping hand to depress the cap 76 to initiate and sustain fluid discharge through the aperture 66.

In a further embodiment, the reservoir 64 may be charged with a rupturable packet, cartridge or other suitable container encasing the irrigant or medicament fluid under pressure. The packet, configured in accordance with the internal dimensions of the reservoir 64 so as to snugly fit therewithin, is inserted into the reservoir so as to engage abutting means provided therein such as the annular flange 90 (FIG. 3) integrated with the handle 62 and defining an included flowpath 92 at least equal in diameter to the conduit 68. The cap 76 in this embodiment is configured so that when substantially fully inserted sufficient pressure is exerted upon the packet either by direct contact or air cushion to cause its rupture. Thus, the proximal end wall of the packet which engages the flange 90 may be designed so as to be rupturable under the pressure conditions extant at substantial cap insertion thereby releasing the autopressured fluid contents. Instead of abutting means, the internal diameter of the reservoir 64 may be necked down proximally so that closure of the cap 76 forces the packet into the smaller space, the resultant increased pressure causing rupture.

In the packet embodiments, flexible tip portions of the type illustrated in FIGS. 4 and 5 are recommended. In FIG. 4, a flexible tip portion 94 is provided with a gate type valve 96 which is normally closed to prevent fluid flow between the conduit sections 98 and 98a, the latter terminating in the outlet aperture 100. The valve 96 is provided with a central horizontal slit to define equal upper and lower sections indicated at 102 and 104 in FIG. 41. In closed position, the valve 96 provides a pressure resistant hermetic seal positionally stable against the pressure exerted by the contents of the reservoir 64. However, when the tip 94 is rotated as indicated by the directional arrow in FIG. 4a, as would be the case when the surface 106 of the tip 94 is pressed against a tooth, flexure of the tip 94 causes the valve 96 to open to the position indicated by the valve sections 102 and 104 in FIG. 4a.

In FIG. 5, an inner surface 108 of the tip 100 is provided with normally closed slits 112, arranged substantially perpendicularly to the surface 108. In closed position, the slits provide a hermetic seal as described. However, when the surface 108 is pressed against a tooth, flexure of the tip 110 as indicated by the directional arrow of FIG. 5a causes the slits 112 to open providing the outlet aperture 112a for the pressurized fluid as indicated in FIG. 5a.

The tip portions as illustrated in FIGS. 5 and 5a are useful in the fluid as well as packet embodiments. In the former case, the cap member is inserted and depressed to the maximum depth permitted by the resultant back pressure. This indicates maximum depth consistent with staple positioning of the cap. In use, the operator need only flex the tip portion in the manner described to initiate and sustain fluid discharge, there being no need to depress the cap.

The tip portions herein may be of hard rubber or similar polymeric material having equivalent resiliency and strength. The material selected should in any event be inert to the contained fluid. The outer surface of the tip should be nonirritating to the gums and tasteless. The tip may be interchangeable and may be attached to the device by simply inserting the proximal end of the handle member thereinto.

The charged fluid may be simply irrigant water or therapeutic agent for treatment of infected gum and may be in liquid or semisolid form.

In a further modification, valve means provided in the tip portion may be manipulated by control means suitably provided in the handle portion and mechanically connected thereto.

In a further preferred embodiment, the handle member is constructed of transparent material, e.g., inert film-forming synthetic organic polymer of types well known in the art enabling visual metering of dosage. Such handle may be graduated, bearing indicia enabling relatively precise assessment of dosage.

A clinical study was conducted to compare the effects on gingival inflammation of use of the device of the invention to apply an isotonic saline solution against using the isotonic saline solution as a mouth rinse. This study was a four week single blind study in which 27 adult subjects participated after having been screened to have a Loe-Silness baseline gingivitis score of at least 1.4. One group (the control group) rinsed their mouths with 20 millileters of isotonic saline solution once daily for two minutes on weekdays under the supervision of a dentist. The other group had 20 milliliters of isotonic saline solution applied by a dentist to the subgingival areas of their mouths with the periodontal irrigation device of the invention, on a daily basis on weekdays. Each of the subjects was evaluated for gingivitis after two weeks and four weeks. The results of the evaluation are as follows:

|  | Mean Gingivitis Scores | | |
| --- | --- | --- | --- |
|  | Baseline | Two Weeks | Four Weeks |
| Mouth rinsing Group (N = 13) | 1.74 | 1.51 | 1.44 |
| Periodontal Irrigating Device Group (N = 14) | 1.80 | 1.19 | 0.81 |

An analysis of variance indicated that subjects who had the isotonic saline solution applied by a dentist to their subgingival areas with the periodontal irrigating device of the invention had significantly less gingivitis ($p = 0.0001$) after two and four weeks than those subject who rinsed their mouths with isotonic saline solution.

The new device provides a means to irrigate the gingival pockets due to its very flexible tip through which the irrigating solution passes that had not been available up to the time of the invention.

We claim:

1. A device for the combined therapeutic and stimulative treatment of the gums comprising an elongated handle member terminating proximally in a flexible tip portion provided with an aperture for the discharge of fluid at low pressure and configured to expedite probing contact of the tip portion with gingival sulcus, a fluid reservoir with a portion thereof movable along the longitudinal axis of the reservoir by an applied force and physically separate from the handle comprising a pressurized or pressurizable unit whose flow rate is controllable to deliver a fluid at a low pressure, and conduit means connecting the tip portion with the fluid reservoir to communicate the fluid from the reservoir to the tip portion.

2. A method for treating gingivitis comprising inserting the tip portion of the device of claim 1 into an affected gingival pocket and irrigating the affected areas with a sufficient amount of fluid at low pressure to cause a beneficial effect.

3. A device for combined therapeutic treatment of the gums comprising
   an elongated handle member terminating proximally in a flexible tip portion provided with one or more apertures for discharge of fluid under pressure and configured to expedite probing contact of the tip with the gingival sulcus,
   a fluid reservoir portion physically separate from the handle member hermetically sealed by a removable insert cap movable along the longitudinal axis of the reservoir portion, and
   a conduit means in communication between the tip portion and the reservoir portion such that movement of the insert cap along the longitudinal axis of the reservoir portion decreases the total volume of the reservoir and correspondingly increases the pressure on the fluid contoured therein.

* * * * *